United States Patent
Syeda-Mahmood et al.

(10) Patent No.: US 9,147,178 B2
(45) Date of Patent: Sep. 29, 2015

(54) DE-IDENTIFICATION IN VISUAL MEDIA DATA

(75) Inventors: Tanveer F. Syeda-Mahmood, Cupertino, CA (US); David J. Beymer, San Jose, CA (US); Omar U. F. Choque, Logan, UT (US); Dulce B. Ponceleon, Palo Alto, CA (US); Dai Shi, Stanford, CA (US)

(73) Assignee: International Business Machines Corporation, Armonk, NY (US)

( * ) Notice: Subject to any disclaimer, the term of this patent is extended or adjusted under 35 U.S.C. 154(b) by 186 days.

(21) Appl. No.: 13/351,141

(22) Filed: Jan. 16, 2012

(65) Prior Publication Data

US 2013/0182006 A1    Jul. 18, 2013

(51) Int. Cl.
G06F 21/00 (2013.01)
G06Q 10/10 (2012.01)
G06F 19/00 (2011.01)
G06F 21/62 (2013.01)
G06Q 50/22 (2012.01)

(52) U.S. Cl.
CPC .............. *G06Q 10/10* (2013.01); *G06F 19/321* (2013.01); *G06F 21/6254* (2013.01); *G06Q 50/22* (2013.01)

(58) Field of Classification Search
USPC .......................................................... 726/26
See application file for complete search history.

(56) References Cited

U.S. PATENT DOCUMENTS

| | | | |
|---|---|---|---|
| 5,442,715 A * | 8/1995 | Gaborski et al. | 382/187 |
| 6,081,620 A * | 6/2000 | Anderholm | 382/194 |
| 7,519,591 B2 | 4/2009 | Landi et al. | |
| 7,970,213 B1 * | 6/2011 | Ruzon et al. | 382/229 |
| 2004/0193901 A1 * | 9/2004 | Bharara | 713/193 |
| 2005/0180645 A1 * | 8/2005 | Hasegawa et al. | 382/239 |
| 2008/0046757 A1 * | 2/2008 | Staddon et al. | 713/189 |
| 2009/0074259 A1 | 3/2009 | Baltatu et al. | |
| 2010/0074525 A1 * | 3/2010 | Drory et al. | 382/176 |
| 2011/0123115 A1 * | 5/2011 | Lee et al. | 382/185 |
| 2011/0242617 A1 * | 10/2011 | King et al. | 358/474 |
| 2012/0033892 A1 * | 2/2012 | Blenkhorn et al. | 382/218 |

(Continued)

FOREIGN PATENT DOCUMENTS

CN    101464951    6/2009
WO    0206948    1/2002

OTHER PUBLICATIONS

"A Visual Method for Capturing and Applying Actionable Templates to Customize Portal Applications," IBM, Prior Art Database, Disclosure No. IPCOM000124657D, (May 3, 2005), 5 pages.

(Continued)

*Primary Examiner* — Joseph P Hirl
*Assistant Examiner* — Chi Nguy
(74) *Attorney, Agent, or Firm* — Jeffrey T. Holman

(57) ABSTRACT

A visual media de-identification system is described. The system includes an image merger and a de-identifying engine. The image merger is configured to merge a sequence of images from a set of visual media data into an averaged image. The de-identifying engine is configured to: bound portions of the averaged image that are determined to be relatively fixed, wherein each bounded portion is identified by a corresponding position in the averaged image; generate a template comprising the bounded portions and the corresponding position for each bounded portion in the averaged image; and de-identify the sequence of images by obfuscating content in the bounded portions.

9 Claims, 7 Drawing Sheets

(56) References Cited

U.S. PATENT DOCUMENTS

2012/0051649 A1* 3/2012 Saund et al. .................. 382/195
2012/0117461 A1* 5/2012 Sata et al. ..................... 715/243

OTHER PUBLICATIONS

Gross et al. "Face De-Identification," Protecting Privacy in Video Surveillance, (2009), 19 pages.
Zhu et al. "An Automatic System to Detect and Extract Text in Medical Images for De-identification," Medical Imaging 2010: Advanced PACS-based Imaging Informatics and Therapeutic Applications, Proceedings of the SPIE, vol. 7628, (2010), 9 pages.
Emam "Heuristics for De-identifying Health Data," IEEE Security and Privacy, vol. 6, Issue 4, (Jul. 2008).
Rashid et al. "Protect Privacy of Medical Informatics Using k-Anonymization Model," The 7th International Conference on Informatics and Systems (INFOS), (Mar. 2010), pp. 1-10.
Machanavajjhala et al. "L-Diversity: Privacy Beyond k-Anonymity," ACM Transactions on Knowledge Discovery from Data (TKDD), vol. 1, Issue 1, (Mar. 2007), 12 pages.

* cited by examiner

DE-IDENTIFICATION IN VISUAL MEDIA DATA

BACKGROUND

Regulatory requirements and business considerations may often require that data be exchanged in a secure manner, particularly in healthcare. The Health Insurance Portability and Accountability Act of 1996 (HIPAA) regulations require secure exchange of data without revealing patient-specific information. Consequently, certain types of data must be modified to obfuscate sensitive or confidential information before being exchanged.

Methods that address de-identification generally address the problems of (1) what should be de-identified, (2) how much should be de-identified, and (3) how it should be de-identified. Various methods of de-identification of documents and metadata fields include built-in code to remove portions marked for de-identification or template-based approaches to redact information from documents in a class of documents. Methods of de-identification have been used for text documents, structured metadata fields such as in Digital Imaging and Communications in Medicine (DICOM) metadata, but de-identification of visual media data when the identification is embedded inside the content can be difficult and time consuming.

SUMMARY

Embodiments of a system are described. In one embodiment, the system is a visual media de-identification system. The system includes: an image merger configured to merge a sequence of images from a set of visual media data into an averaged image; and a de-identifying engine configured to: bound portions of the averaged image that are determined to be relatively fixed, wherein each bounded portion is identified by a corresponding position in the averaged image; generate a template comprising the bounded portions and the corresponding position for each bounded portion in the averaged image; and de-identify the sequence of images by obfuscating content in the bounded portions. Other embodiments of the system are also described.

Embodiments of a computer program product are also described. In one embodiment, the computer program product includes a computer readable storage medium to store a computer readable program, wherein the computer readable program, when executed by a processor within a computer, causes the computer to perform operations for de-identification of visual media data. The operations include: merging a sequence of images from a set of visual media data into an averaged image; bounding portions of the averaged image that are determined to be relatively fixed, wherein each bounded portion is identified by a corresponding position in the averaged image; generating a template comprising the bounded portions and the corresponding position for each bounded portion in the averaged image; and de-identifying the sequence of images by obfuscating content in the bounded portions. Other embodiments of the apparatus are also described.

BRIEF DESCRIPTION OF THE DRAWINGS

Throughout the description, similar reference numbers may be used to identify similar elements.

DETAILED DESCRIPTION

Figure 1:
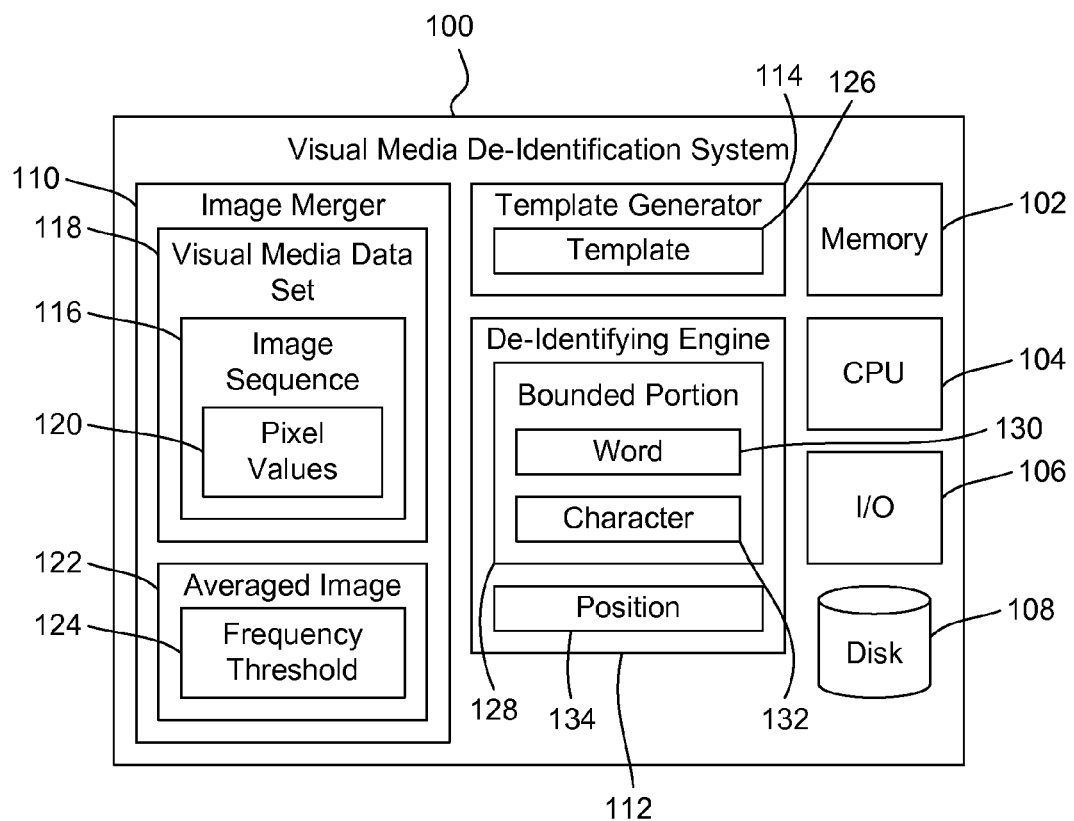
FIG. 1 depicts a schematic diagram of one embodiment of a visual media de-identification system.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments present a system and method for de-identifying confidential or sensitive information from visual media data. More specifically, the system merges a sequence of images from a set of visual media data and automatically identifies locations in the averaged image that are likely to contain text. A user may manually refine the selected portions of the averaged image to determine which portions contain sensitive or confidential information, and the system generates a template from the averaged image and selected portions that may be applied to sequences of images in the set of visual media data for obfuscating confidential information in each image sequence.

Some conventional methods for determining what to de-identify in text data include: (i) manually marking sensitive regions using redaction tools, and regions in a solution document are manually identified for deletion; (ii) automatic de-identification in which text mining methods are used to spot sensitive pieces of text such as names, dates, and addresses, either within structured data fields or in free text; and (iii) fixed known fields in structured data—for example, names, dates, and addresses may be cleaned by code specifically structured for such fields. Conventional methods also manually mark regions for determining how much to de-identify. The conventional methods for how content is de-identified include either built-in code to remove the identified portions or using a template-based approach. In the conventional template-based approach, the template is manually created by highlighting regions to redact in a sample document of a given class. This approach may be useful when a limited number of forms are available.

In images and videos, sensitive information could be embedded in a variety of layouts, creating many form types. For DICOM images and videos in particular, the patient-specific data seen in an image will vary with the modality type (e.g., echo vs. angiogram), the manufacturer (different manufacturers may show different information on their screens), and the examination itself, that is further dependent on a corresponding disease and its findings. The combination of these factors results in a large number of form types to be seen in visual media data (including frames from videos), such that manual learning of templates becomes very cumbersome and cost ineffective. For example, in a typical echo recording, as many as 50 different form types may be present corresponding to over approximately 146 measurements recorded by a sonographer, depending on the disease. Consequently, a system capable of at least semi-automatically generating templates for de-identifying visual media data may provide quick and efficient de-identification various types of images and video. In some embodiments, the template may be learned from sample collections of visual media data sources. Additionally, correction or modification of the template may be implemented through a semi-automatic process, as described herein. Furthermore, during the training stage to form the template, the template (or a preliminary version of the template) may be applied to candidate regions in images in order to identify some or all possible occurrences of image/textual content within the identified bounding boxes of the template.

Figure 7:
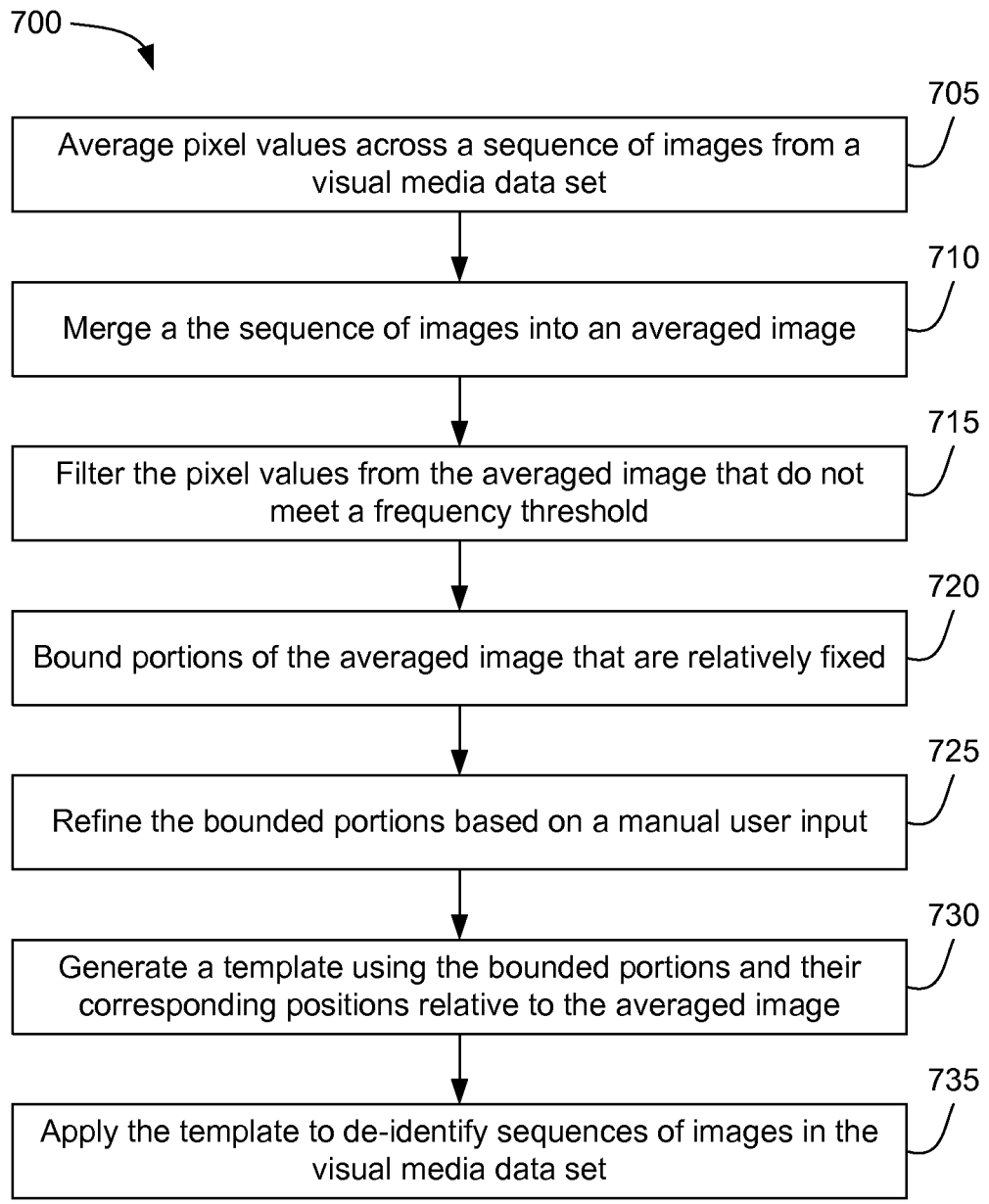
FIG. 7 depicts a flowchart diagram of one embodiment of a method for de-identification of visual media data.

FIG. 1 depicts a schematic diagram of one embodiment of a visual media de-identification system 100. The depicted visual media de-identification system 100 includes various components, described in more detail below, that are capable of performing the functions and operations described herein. In one embodiment, at least some of the components of the de-identification system 100 are implemented in a computer system. For example, the functionality of one or more components of the de-identification system 100 may be implemented by computer program instructions stored on a computer memory device 102 and executed by a processing device 104 such as a CPU. The de-identification system 100 may include other components, such as input/output devices 106, a disk storage drive 108, an image merger 110, a de-identifying engine 112, and a template generator 114. Some or all of the components of the visual media de-identification system 100 may be stored on a single computing device or on a network of computing devices, including a wireless communication network. The de-identification system 100 may include more or fewer components or subsystems than those depicted herein. In some embodiments, the de-identification system 100 may be used to implement the methods described herein as depicted in FIG. 7.

In one embodiment, the image merger 110 receives a sequence 116 of images from a set 118 of visual media data. In some embodiments, the set 118 of visual media data may include images or video captured using medical equipment, including ultrasound images, echocardiogram images, angiogram images, or any other visual media. In other embodiments, the set 118 of visual media data may include images or video captured or generated using equipment for other applications. Each image sequence 116 may include many images. For example, a video may include many individual image frames captured per second.

In some embodiments, the image merger 110 is configured to receive sequences 116 of images from multiple sets 118 of visual media data. Each set 118 of visual media data may correspond to a different machine type. The sets 118 of visual media data may be grouped according to predetermined categories, such as machine type, location, hospital, department, or any type of categorization system for which the image sequences 116 in each visual media data set 118 have certain visual characteristics in common with the other image sequences 116 in the corresponding visual media data set 118, such as geographic layout, textual similarities, or other characteristics.

In one embodiment, the image merger 110 merges the images in the image sequence 116 by averaging pixel values 120 for each of the images across the entire image sequence 116. This obtains an averaged image 122 with pixel values 120 averaged across all of the images in the image sequence 116. In one embodiment, because the averaged image 122 contains averaged pixel values 120, the averaged image 122 may display only pixels that are constant or fixed across all or most of the images in the image sequence 116. The algorithm used to average the pixel values 120 may be based on the intensity, color value, saturation, and/or other characteristics of the pixels. In some embodiments, pixels that do not meet a predetermined frequency threshold 124 across the images in the image sequence 116 are filtered from the averaged image 122. The frequency threshold 124 may be any value that allows the system 100 to sufficiently recognize text fields in the image sequence 116.

In one embodiment, the resulting pixel values 120 in the averaged image 122 are displayed with the averaged intensity of the pixel values 120 at each pixel location. Consequently, pixels that do not have a constant active value may be displayed in the averaged image 122 as dark pixels, depending on the color scheme of the images. For example, an averaged image 122 from an ultrasound image sequence 116 includes black pixel values 120 for pixels that are not constant across all or most of the images, while pixels that have a relatively constant active value across all or most of the images have a white or bright pixel value 120. Any fixed text for the images may then be maintained in the averaged image 122 because the pixel values 120 are constant across all images.

The de-identifying engine 112 is configured to bound portions in the averaged image 122 that are determined to be relatively fixed. In one embodiment, the bounded portions 128 correspond to bright pixel values 120 in the averaged image 122. The de-identifying engine 112 may retain the bounded portions 128 that have a certain size or be within a certain distance of other bounded portions 128, and may discard the bounded portions 128 that do not meet such requirements.

In one embodiment, the de-identifying engine 112 is configured to bound connected components from the averaged image 122 to find characters 132 or potential characters in the averaged image 122 and to produce a character image. The connected components may be pixel regions in which all of the included pixels have a bright pixel value 120. The system 100 may also be configured to bound words 130 from the averaged image 122 using optical character recognition (OCR) software to recognize potential words 130 and text in the averaged image 122 to produce a word image. A word 130, as described herein, may include any combination of one or more characters 132. Based on the word image and the character image, the de-identifying engine 112 may then retain bounded portions 128 in which a certain, predetermined percentage of the bounded characters 132 from the character image and the bounded words 130 from the word image overlap. Consequently, bounded connected components that overlap to a large extent with bounded words 130 or word components may be retained in a phrase image.

The template generator 114 uses the phrase image to generate a template 126 for use with de-identification of image sequences 116 for a particular visual media data set 118. The bounded portions 128 in the phrase image may be included in the template 126 with the corresponding position 134 of each bounded portion 128 in the averaged image 122. In some embodiments, the bounded portions 128 may be refined before generating the template 126 based on a manual user input. In some embodiments, aspects of the refinement operations may be automatic or semi-automatic based on further review of pixel averages and/or user selections. Additionally, in some embodiments, the template may be further refined some time after the template is generated and initially put into use. The content in the bounded portions 128 may be obfuscated in each of the image sequences 116 in the visual data set 118 using the template 126.

In some embodiments, the image content and the textual content within the bounded regions is extracted. The textual information is then identified and grouped in semantic entities by an analysis of both the bounding boxes of characters and words. In other embodiments, other operations and/or analysis may be implemented to extract and identify textual content.

Figure 2:
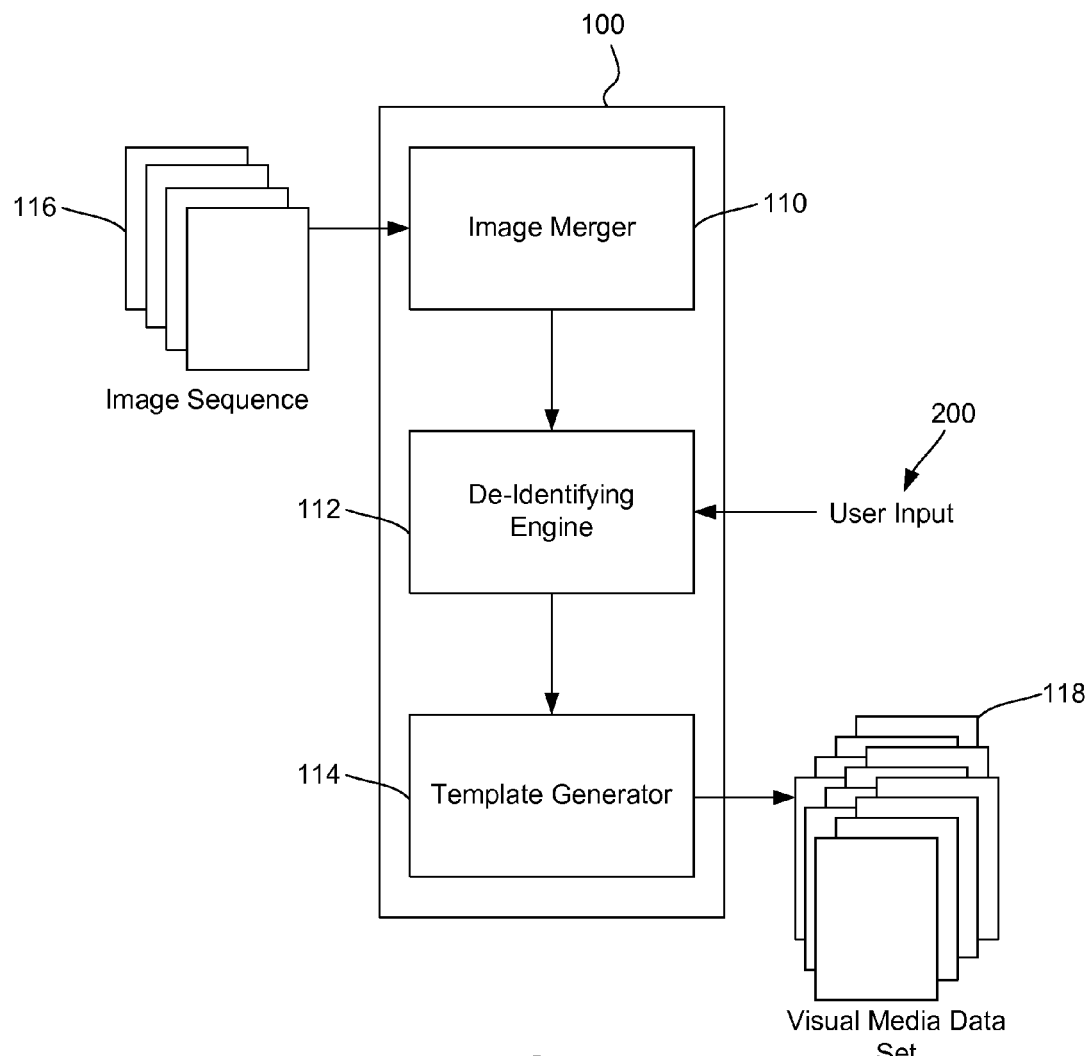
FIG. 2 depicts a schematic diagram of one embodiment of the visual media de-identification system of FIG. 1.

FIG. 2 depicts a schematic diagram of one embodiment of the visual media de-identification system 100 of FIG. 1. The de-identification system 100 receives an image sequence 116 corresponding to a visual media data set 118. The de-identification system 100 includes an image merger 110 to merge the images from the image sequence 116 into an averaged image 122. The image merger 110 may use any method to merge the images from the image sequence 116 to create the averaged image. The averaged image may display components that are relatively fixed or constant in all or some of the images in the image sequence 116.

After merging the images in the image sequence 116 into an averaged image 122, the de-identifying engine 112 finds portions of the averaged image 122 that are likely to contain text or words 130 and marks the locations of the text using bounding boxes or another visual bounding method. The bounded portions 128 may be refined manually based on a user input 200 to either keep or remove bounding boxes in the averaged image 122.

The template generator 114 then uses the averaged image 122 to generate a de-identification template 126 based on the bounded portions 128 in the averaged image 122. The template 126 may be used to de-identify the sequence 116 of images by obfuscating content in the sequence 116 of images corresponding to the bounded portions 128 and their respective positions 134 in the averaged image 122. The content may be obfuscated by removing the content from the images, replacing the content with other content, blurring the content, or otherwise modifying the content or a portion of the content. In some embodiments, the content may be obfuscated using several obfuscation methods to ensure complete de-identification. In some embodiments, the content that is obfuscated may be visible to certain users according to viewing rights for the content. The system 100 is configured to establish viewing rights for the bounded portions 128 based on the user input 200, such that the viewing rights determine when content of the bounded portions 128 is viewable to a given user. For example, the content for a given region may be visible to one user, but obfuscated for another user. Additionally, different content in the images may include different viewing rights for users.

The template 126 may also be used to de-identify other image sequences 116 in the visual media data set 118. In one embodiment, the image sequences 116 in the visual media data set 118 have similar or same geographic layouts, such that the locations of the bounded portions 128 in the template 126 match up with the locations of sensitive data in each of the images in the other image sequences 116, which may allow the image sequences 116 in the visual media data set 118 to be de-identified quickly and effectively.

Figure 3:
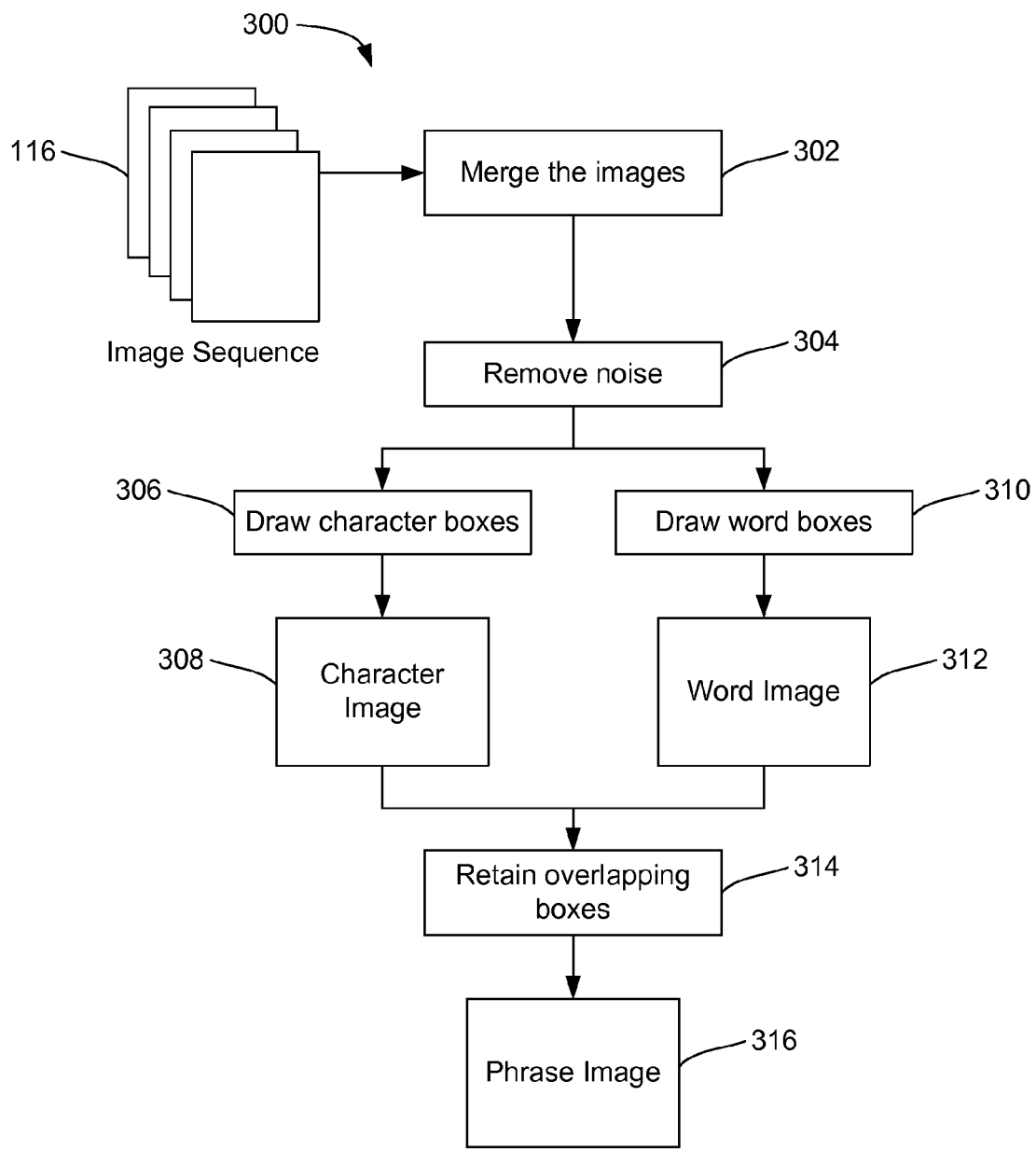
FIG. 3 depicts a flowchart diagram of one embodiment of a method for generating a visual media de-identification template.

FIG. 3 depicts a flowchart diagram of one embodiment of a method 300 for generating a visual media de-identification template 126. Although the method 300 is described in conjunction with the de-identification system 100 of FIG. 1, embodiments of the method 300 may be implemented with other types of de-identification systems 100.

In one embodiment, the de-identification system 100 merges 302 a sequence 116 of images into a single averaged image 122. For example, the averaged image 122 may be obtained in any manner capable of depicting the sequence 116 of images in one image having pixel values 120 averaged over all images in the image sequence 116. The system 100 may also remove noise 304 from the averaged image 122 to allow the de-identification system 100 to more easily determine portions of the averaged image 122 to be bounded.

The de-identification system 100 then draws 306 character bounding boxes 400 around connected components in the averaged image 122, or in a copy of the averaged image 122 to obtain a character image 308. The de-identification system 100 also draws 310 word bounding boxes around words 130 in the averaged image 122, or in a copy of the averaged image 122 to obtain a word image 312. In various embodiments, the de-identification system 100 may perform the automated bounding operations in simultaneous processes or in sequential processes.

The resulting character image and word image 312 may then be used to find the most likely portions of the averaged image 122 to contain text. In one embodiment, the de-identification system 100 retains 314 bounded regions that include one or more character boxes that overlap either fully or partially with one or more word box. For example, a plurality of character boxes that combined, overlap with most or all of a word box may cause the de-identification system 100 to retain the bounding region corresponding to the character boxes and word box. The percentage of overlap between character boxes and word boxes may allow for some error in drawing the bounding boxes 400 in both the character image and the word image 312 while still maintaining a high likelihood that the retained bounded regions contain text. In some embodiments, the de-identification system 100 may define phrases based on the distance between bounding regions. A phrase image 316 may be created using the bounding regions resulting from retaining the overlapping character/word boxes. The phrase image 316 may be used to generate the template 126 for de-identifying the sequences 116 of images or other sequences 116 of images.

Figure 4:
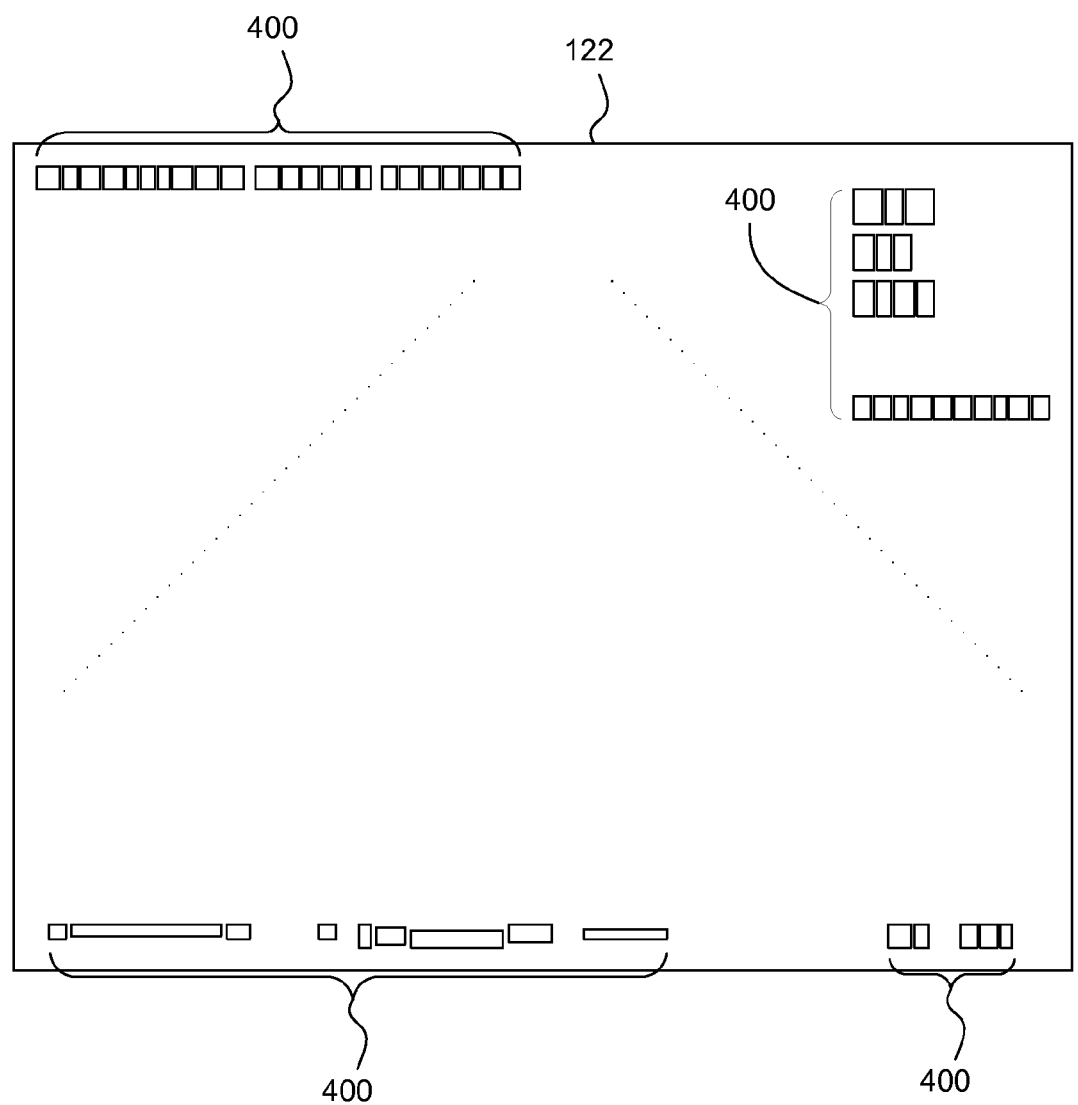
FIG. 4 depicts a schematic diagram of one embodiment of the averaged image of FIG. 1.

FIG. 4 depicts a schematic diagram of one embodiment of the averaged image 122 of FIG. 1. While the de-identification system 100 is described herein in conjunction with the averaged image 122 of FIG. 4, the de-identification system 100 may be used in conjunction with any averaged image 122.

In one embodiment, the de-identification system 100 finds connected components in the averaged image 122 and draws bounding boxes 400 around the connected components. The connected components may be text characters 132, image artifacts, or other regions with multiple active pixel regions connected in a group. A character bounding algorithm may draw the bounding boxes 400 around connected components that are larger than a predetermined size or meet some other threshold, which may help reduce error in detecting characters 132 in the averaged image 122. Components or pixels in the averaged image 122 that do not meet the threshold may be left in the averaged image 122 or may be removed from the image to remove noise or unnecessary components. The bounding boxes 400 drawn around connected components may indicate a clear visual separation between connected components in the averaged image 122 by leaving a space between the bounding boxes 400.

In one embodiment, a user may manually refine the placement or number of bounding boxes 400 in the character image 308 produced when bounding connected components in the averaged image 122. The user may remove bounding boxes 400 that are clearly seen by the user to be non-character components. Alternatively, the user may manually draw boxes around connected components that the de-identification system 100 may have missed.

Figure 5:
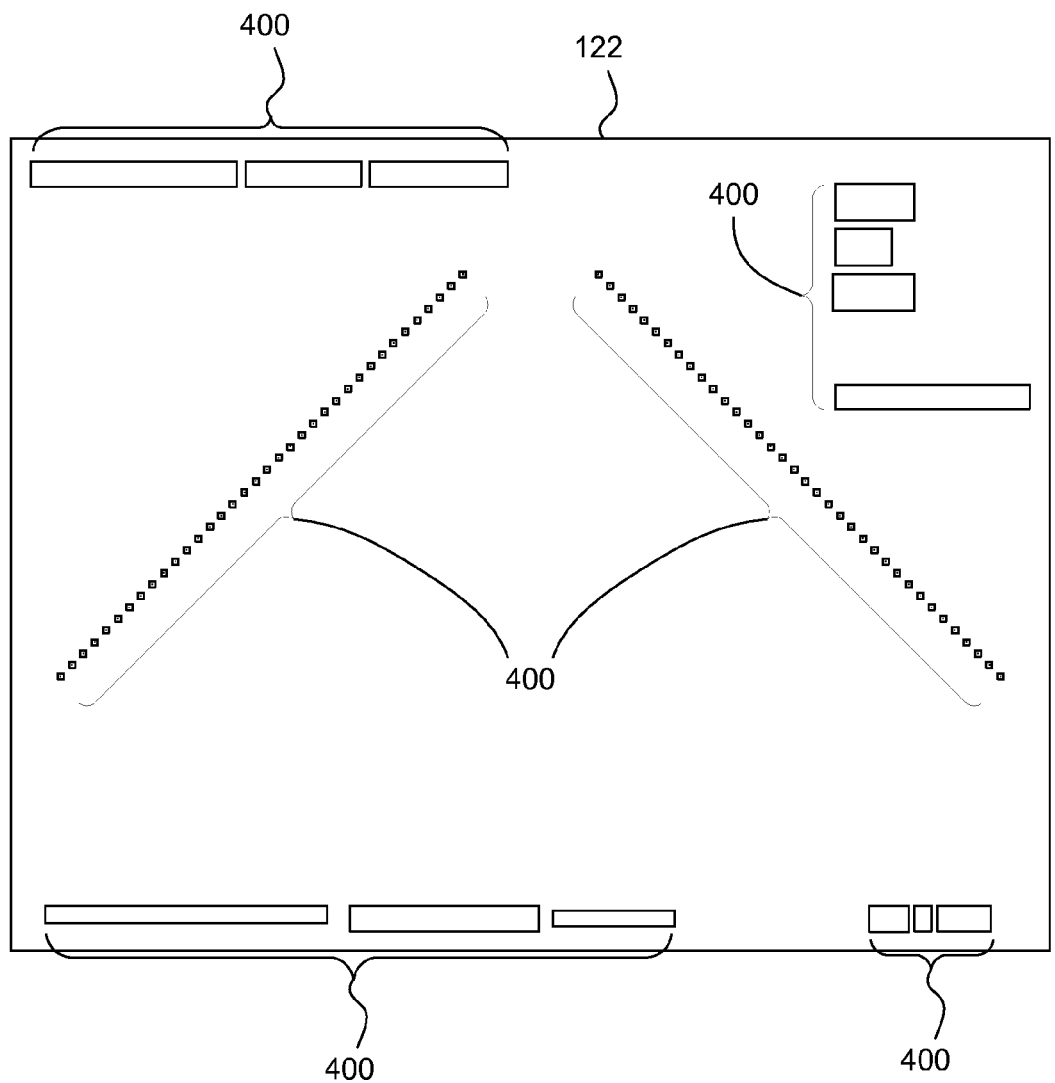
FIG. 5 depicts a schematic diagram of one embodiment of the averaged image of FIG. 1.

FIG. 5 depicts a schematic diagram of one embodiment of the averaged image 122 of FIG. 1. While the de-identification system 100 is described herein in conjunction with the averaged image 122 of FIG. 5, the de-identification system 100 may be used in conjunction with any averaged image 122.

In one embodiment, the de-identification system 100 finds words 130 in the averaged image 122 and draws bounding boxes 400 around the words 130 or regions likely to include text. The de-identification system 100 may use an OCR engine to find text regions. The OCR engine may determine a confidence value that each region in the averaged image 122 has text. If the confidence value meets a certain threshold, the region is considered a candidate and a bounding box 400 is drawn for the region, and the resulting bounding boxes 400 make up the word image 312 for the averaged image 122.

In one embodiment, a user may manually refine the placement or number of bounding boxes 400 in the word image 312 produced when bounding text regions in the averaged image 122. The user may remove bounding boxes 400 that are clearly seen by the user to be non-word or text components. Alternatively, the user may manually draw boxes for regions that the de-identification system 100 may have missed.

Figure 6:
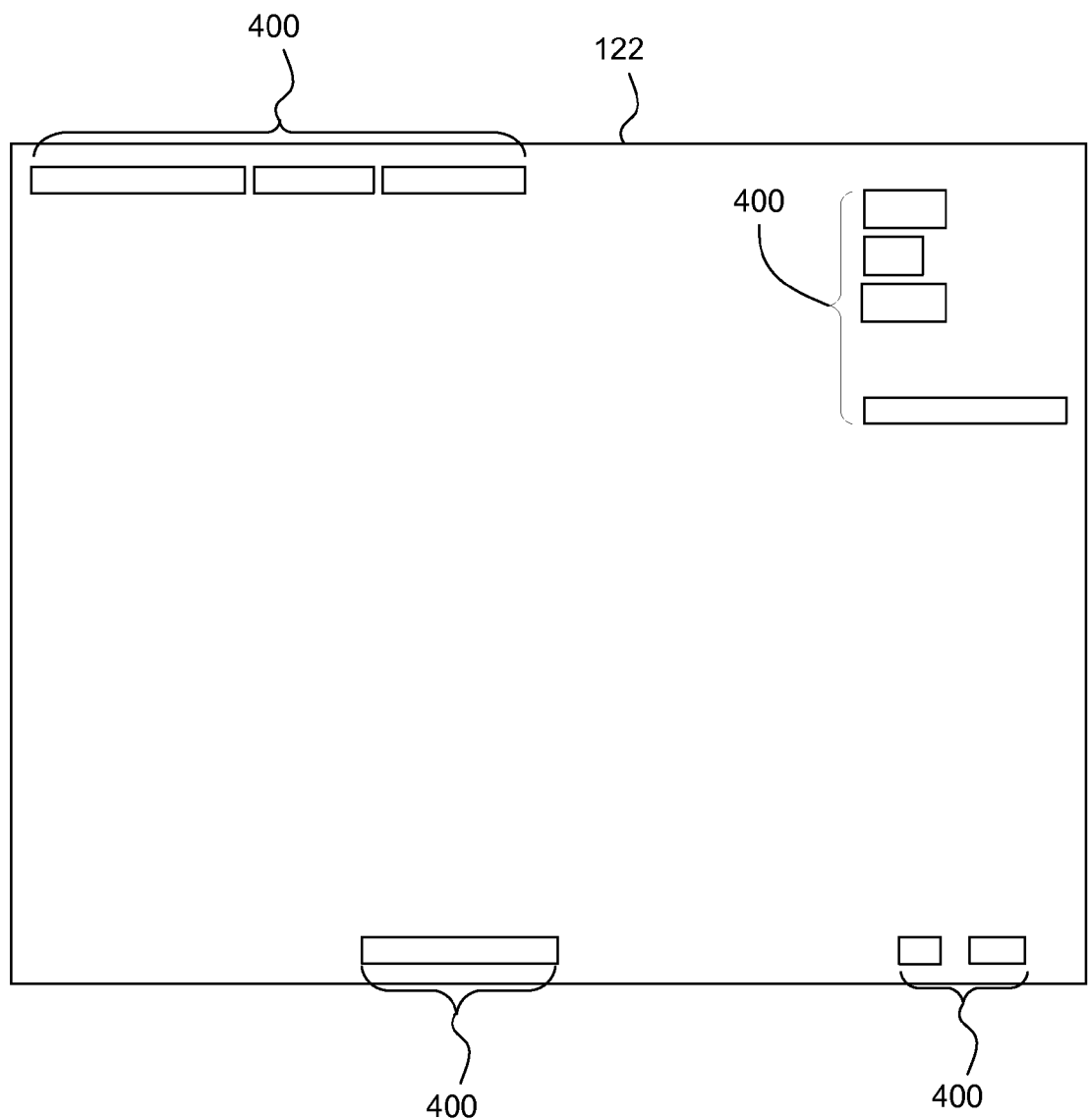
FIG. 6 depicts a schematic diagram of one embodiment of the visual media de-identification template of FIG. 1.

FIG. 6 depicts a schematic diagram of one embodiment of a visual media de-identification template 126. While the de-identification system 100 is described herein in conjunction with the averaged image 122 of FIG. 6, the de-identification system 100 may be used in conjunction with any averaged image 122.

In some embodiments, the de-identification system 100 may draw bounding boxes 400 around components in the word image 312 that are not bounded in the character image 308. Conversely, the de-identification system 100 may draw bounding boxes 400 around components in the character image 308 that are not bounded in the word image 312. By comparing the character image 308 with the word image 312, the de-identification system 100 may be able to determine which boxes most likely contain text.

The de-identification system 100 may retain bounding boxes 400 from the character image 308 that overlap with bounding boxes 400 from the word image 312. In some embodiments, one or more character boxes may overlap with one or more word boxes. For example, a single character box may overlap fully or substantially fully with a single word box, such that the de-identification system 100 may retain the character box or word box, or may generate a new bounded region that encompasses the combined area of both the character box and the word box. In another example, a plurality of character boxes may overlap fully or substantially fully with a single word box, such that the de-identification system 100 may retain the character boxes, word box, or a new bounded region that encompasses the combined area of all character boxes and the word box. In another example, a plurality of character boxes may overlap fully or substantially fully with a plurality of word boxes, such that the de-identification system 100 may retain some or all of the character boxes, word boxes, or one or more bounded regions that encompass the combined area of the character boxes and word boxes. The de-identification system 100 may retain bounded regions according other combinations of character boxes and word boxes or other embodiments not described herein.

The bounded regions retained by the de-identification system 100 may then be used to generate the de-identification template 126. The positions 134 of the bounded regions in the phrase image 316—which may be the averaged image 122 with bounding boxes 400 drawn in certain regions of the averaged image 122—may define portions of the template 126 in which content is to be obfuscated. When the template 126 is applied to images in an image sequence 116, the de-identification system 100 may look for regions in the images that correspond to the positions 134 of the bounded portions 128 of the template 126 and automatically obfuscate the content of the regions in the images. In some embodiments, the template 126 may be applied to streaming media, such that live video captures may be processed with the template 126 to remove sensitive data from the live video.

FIG. 7 depicts a flowchart diagram of one embodiment of a method 700 for de-identification of visual media data. Although the method 700 is described in conjunction with the de-identification system 100 of FIG. 1, embodiments of the method 700 may be implemented with other types of de-identification systems 100.

In one embodiment, the de-identification system 100 merges 710 a sequence 116 of images from a set 118 of visual media data into an averaged image 122. The system 100 may create the averaged image 122 by averaging 705 pixel values 120 across all images in the image sequence 116 and filtering 715 the pixel values 120 from the averaged image 122 that do not meet a predetermined frequency threshold 124.

In one embodiment, the system 100 bounds 720 portions of the averaged image 122 that are determined to be relatively fixed. Each bounded portion 128 may be identified by a corresponding position 134 in the averaged image 122. In one embodiment, bounding portions of the averaged image 122 includes bounding connected components from the averaged image 122 to find characters 132 to produce a character image 308. Bounding portions of the averaged image 122 also includes bounding words 130 from the averaged image 122 to produce a word image 312. This may include analyzing a portion of the averaged image 122 to obtain a confidence level that the analyzed portion contains text. The analyzed portions may be analyzed by an OCR engine. In one embodiment, the OCR engine is specifically tailored for use with the de-identification system 100. The system 100 may establish the analyzed portion as a word candidate in response to determining that the confidence level meets a word threshold. The system 100 may then retain bounded portions 128 in which a predetermined percentage of bounded characters 132 from the character image 308 and bounded words 130 from the word image 312 overlap. In one embodiment, the system 100 merges bounded portions 128 within a predetermined average distance of each other to form a phrase. The phrases may be bounded together to make obfuscation of a bounded region more efficient.

The system 100 may then generate a template 126 that includes the bounded portions 128 and the corresponding position 134 for each bounded portion 128 in the averaged image 122, such that the positions 134 of the bounded portions 128 in the averaged image 122 are retained in the template 126. In some embodiments, the averaged image 122 with the bounded portions 128 may be used as the template 126. In other embodiments, a new template file may be generated based on the averaged image 122. In one embodiment, the bounded portions 128 in the template 126 or averaged image 122 may be refined 725 manually based on a user input 200. The user may determine that a bounded portion 128 included in the template 126 or averaged image 122 does not correspond to data that is sensitive or confidential, and may remove the bounding box 400 from the template 126. In another embodiment, the user determines that a portion of the averaged image 122 that corresponds to sensitive data was not bounded, and the user may manually draw a bounding box 400 around the sensitive portion in the template 126 or averaged image 122. The user may also establish viewing rights for bounded portions 128 of the averaged image 122 that determine when the bounded portions 128 are viewable to a given user.

The template 126 may then be applied 735 to de-identify the sequence 116 of images used to create the template 126 by obfuscating the content in the images in locations that correspond to the bounded portions 128 of the template 126. This may allow for consistent obfuscation across all images in the image sequence 116. In one embodiment, the template 126 is then used to de-identify other image sequences 116 in the visual media data set 118. The other image sequences 116 may share similar characteristics with the image sequence 116 used to generate 730 the template 126, such as the geographic location of text, objects, or other components within each image. In some embodiments, the system 100 may generate a template 126 for each visual media data set 118, such that the system 100 is able to automatically de-identify image sequences 116 for each different visual media data set 118.

While the system 100 and method presented herein are described in relation to de-identifying visual media data, the system 100 and method may also be used to de-identify textual data or other types of data.

An embodiment of a phrase matching system 100 includes at least one processor coupled directly or indirectly to memory elements through a system bus such as a data, address, and/or control bus. The memory elements can include local memory employed during actual execution of the program code, bulk storage, and cache memories which provide temporary storage of at least some program code in order to reduce the number of times code must be retrieved from bulk storage during execution.

It should also be noted that at least some of the operations for the methods may be implemented using software instructions stored on a computer useable storage medium for execution by a computer. As an example, an embodiment of a computer program product includes a computer useable storage medium to store a computer readable program that, when executed on a computer, causes the computer to perform operations, including an operation to extract information from electronic documents.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Embodiments of the invention can take the form of an entirely hardware embodiment, an entirely software embodiment, or an embodiment containing both hardware and software elements. In one embodiment, the invention is implemented in software, which includes but is not limited to firmware, resident software, microcode, etc.

Furthermore, embodiments of the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The computer-useable or computer-readable medium can be an electronic, magnetic, optical, electromagnetic, infrared, or semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

Input/output or I/O devices (including but not limited to keyboards, displays, pointing devices, etc.) can be coupled to the system either directly or through intervening I/O controllers. Additionally, network adapters also may be coupled to the system to enable the data processing system to become coupled to other data processing systems or remote printers or storage devices through intervening private or public networks. Modems, cable modems, and Ethernet cards are just a few of the currently available types of network adapters.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A computer program product, comprising:
a computer readable storage device to store a computer readable program, wherein the computer readable program, when executed by a processor within a computer, causes the computer to perform operations for de-identification of visual media data, the operations comprising:
merging a sequence of images from a set of visual media data into an averaged image;
bounding portions of the averaged image that are determined to be relatively fixed, wherein each bounded portion corresponds to identification information located at a relatively fixed position in a plurality of images in the sequence of images, wherein each bounded portion is identified by a corresponding position in the averaged image, and wherein bounding portions of the averaged image that are determined to be relatively fixed further comprises:
bounding connected components from the averaged image to find characters and to produce a character image;
bounding words from the averaged image to produce a word image, wherein bounding words from the averaged image further comprises:
analyzing a portion of the averaged image to obtain a confidence level that the analyzed portion contains text; and
establishing the analyzed portion as a word candidate in response to determining that the confidence level meets a word threshold;
retaining bounded portions in which a predetermined percentage of bounded characters from the character image and bounded words from the word image overlap;
generating a template for de-identifying the sequence of images, wherein the template comprises the bounded portions and the corresponding position for each bounded portion in the averaged image;
de-identifying the sequence of images by obfuscating content in the bounded portions; and
establishing viewing rights for the bounded portions, wherein at least two of the bounded portions comprise different viewing rights, wherein content in a first bounded portion is visible only to a first set of users, and content in a second bounded portion is visible only to a different, second set of users.

2. The computer program product of claim 1, wherein merging the sequence of images further comprises:
averaging pixel values across all images in the sequence of images to obtain the averaged image; and
filtering the pixel values from the averaged image that do not meet a predetermined frequency threshold.

3. The computer program product of claim 1, wherein the computer readable program, when executed on the computer, causes the computer to perform additional operations, comprising:
applying the template to de-identify other sequences of images in the set of visual media data.

4. The computer program product of claim 1, wherein the computer readable program, when executed on the computer, causes the computer to perform additional operations, comprising:
merging bounded portions within a predetermined average distance of each other to form a phrase.

5. The computer program product of claim 1, wherein the computer readable program, when executed on the computer, causes the computer to perform additional operations, comprising:
refining the bounded portions of the averaged image based on a user input.

6. A visual media de-identification system, comprising:
an image merger configured to merge a sequence of images from a set of visual media data into an averaged image; and
a de-identifying engine configured to:
bound portions of the averaged image that are determined to be relatively fixed, wherein each bounded portion corresponds to identification information located at a relatively fixed position in a plurality of images in the sequence of images, wherein each bounded portion is identified by a corresponding position in the averaged image, and wherein bounding portions of the averaged image that are determined to be relatively fixed further comprises:
bounding connected components from the averaged image to find characters and to produce a character image;
bounding words from the averaged image to produce a word image, wherein bounding words from the averaged image further comprises:
analyzing a portion of the averaged image to obtain a confidence level that the analyzed portion contains text; and
establishing the analyzed portion as a word candidate in response to determining that the confidence level meets a word threshold;
retaining bounded portions in which a predetermined percentage of bounded characters from the character image and bounded words from the word image overlap;
generate a template for de-identifying the sequence of images, wherein the template comprises the bounded portions and the corresponding position for each bounded portion in the averaged image;
de-identify the sequence of images by obfuscating content in the bounded portions; and
establish viewing rights for the bounded portions, wherein at least two of the bounded portions comprise different viewing rights, wherein content in a first bounded portion is visible only to a first set of users, and content in a second bounded portion is visible only to a different, second set of users.

7. The system of claim 6, wherein the image merger is further configured to:
average pixel values across all images in the sequence of images to obtain the averaged image; and
filter the pixel values from the averaged image that do not meet a predetermined frequency threshold.

8. The system of claim 6, further comprising a template generator configured to:
apply the template to de-identify other sequences of images in the set of visual media data.

9. The system of claim 6, wherein the de-identifying engine is further configured to:
refine the bounded portions of the averaged image based on a user input.

* * * * *